(12) United States Patent
Menon

(10) Patent No.: US 7,136,691 B2
(45) Date of Patent: Nov. 14, 2006

(54) BIOMEDICAL ELECTRODES

(75) Inventor: Vinod P. Menon, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 495 days.

(21) Appl. No.: 10/655,329

(22) Filed: Sep. 4, 2003

(65) Prior Publication Data

US 2004/0082843 A1     Apr. 29, 2004

(51) Int. Cl.
*A61B 5/04* (2006.01)
(52) U.S. Cl. .................................. 600/395; 500/396
(58) Field of Classification Search ......... 600/395–397
See application file for complete search history.

(56) References Cited

U.S. PATENT DOCUMENTS

| | | | |
|---|---|---|---|
| 4,674,512 A | | 6/1987 | Rolf |
| 4,846,185 A | | 7/1989 | Karim |
| 4,947,847 A | * | 8/1990 | Nakao et al. ............... 600/391 |
| 5,354,790 A | * | 10/1994 | Keusch et al. .............. 600/395 |
| 5,660,178 A | | 8/1997 | Kantner et al. |
| 5,779,632 A | | 7/1998 | Dietz et al. |
| 5,797,902 A | | 8/1998 | Netherly |
| 5,985,990 A | | 11/1999 | Kantner et al. |
| 6,232,366 B1 | * | 5/2001 | Wang et al. ................. 600/391 |
| 6,731,965 B1 | * | 5/2004 | Menon et al. .............. 600/396 |
| 2002/0188035 A1 | | 12/2002 | Uy et al. |
| 2003/0045788 A1 | | 3/2003 | Menon et al. |
| 2004/0082843 A1 | | 4/2004 | Menon |

FOREIGN PATENT DOCUMENTS

WO     WO 02/089906     11/2002

* cited by examiner

*Primary Examiner*—Lee S. Cohen
(74) *Attorney, Agent, or Firm*—Daniel R. Pastirik

(57) ABSTRACT

A biomedical electrode is provided wherein the electrode comprises a conductor in contact with a conductive medium, the conductor comprises an electrically conductive surface comprising an active source of silver and the conductive medium comprises a peroxide scavenger. The biomedical electrode typically will include a non-conductive backing having a first side comprising a first major surface and a second side comprising a second major surface, the electrically conductive surface being associated with the second major surface of the non-conductive backing, and the conductive medium comprises an electrically conductive adhesive associated with the conductive substrate, the electrically conductive adhesive being a pressure sensitive adhesive comprising the at least one peroxide scavenger. A method for the manufacture of the foregoing electrodes is also provided.

31 Claims, 4 Drawing Sheets

BIOMEDICAL ELECTRODES

The present invention relates to biomedical electrodes and to methods for making such electrodes. More particularly, the present invention relates to biomedical electrodes comprising a conductor having an electrically conductive surface in association with a conductive medium and a peroxide scavenger.

BACKGROUND OF THE INVENTION

Modern medicine employs many medical procedures where electrical signals or currents are received from or delivered to a patient's body. The interface between medical equipment used in these procedures and the skin of the patient usually includes a biomedical electrode. Such an electrode typically includes a conductor connected electrically to the equipment and a conductive medium adhered to or otherwise in contact with the patient's skin. Biomedical electrodes have been included as a part of therapeutic as well as diagnostic medical procedures and equipment.

Therapeutic devices and procedures using those devices make use of biomedical electrodes. For example, such electrodes are employed in transcutaneous electronic nerve stimulation (TENS) devices for pain management; neuromuscular stimulation (NMS) techniques for treating conditions such as scoliosis; defibrillation electrodes for dispensing electrical energy to a chest cavity to defibrillate the heart; and dispersive electrodes to receive electrical energy dispensed into an incision made during electrosurgery.

Diagnostic procedures that make use of biomedical electrodes include electrocardiography for monitoring heart activity and diagnosing heart abnormalities. Examples of diagnostic biomedical electrodes include those described in U.S. Pat. No. 4,352,359 to Larimore; U.S. Pat. No. 4,524,087 to Engel; U.S. Pat. No. 4,539,996 to Engel; U.S. Pat. No. 4,554,924 to Engel; U.S. Pat. No. 4,848,348 to Carim; U.S. Pat. No. 4,848,353 to Engel; U.S. Pat. No. 5,012,810 to Strand et al.; U.S. Pat. No. 5,133,356 to Bryan et al.; U.S. Pat. No. 5,215,087 to Anderson et al.; and U.S. Pat. No. 5,296,079 to Duan et al.

For diagnostic applications, non-polarizable electrodes, and in particular electrodes comprised of silver and/or silver chloride, have become the current collectors of choice because of their high electrical stability. In low-cost versions, such electrodes are often coated in thin sections onto an insulating backing from a conductive ink containing silver/silver chloride particles and a polymeric binder. While silver/silver chloride electrodes are resistant to corrosive attack and generally have a long shelf-life, under certain gel conditions (e.g., at a low pH in conjunction with a high water content and high chloride concentration), they can undergo accelerated corrosion and exhibit premature electrical failure. Attempts to address the problem of undesired corrosion and failure include the use of sacrificial anodes interwoven into an electrode assembly and electrically connected to a current collector. While functional, the use of sacrificial anodes is generally not cost-effective due to added material costs and certain design constraints. Another method for inhibiting corrosion has been the addition of organic agents as corrosion retarding agents to the silver/silver chloride matrix. The use of corrosion retarding agents is disclosed in copending and coassigned U.S. Patent Application 20030045788 by Menon et al, entitled "Corrosion Prevention In Biomedical Electrodes."

Additionally, other materials have been proposed as alternatives for traditional silver and/or silver chloride electrode materials. Exemplary of such alternate materials include those comprised of titanium hydride and certain carbon-containing materials. However, electrodes incorporating these alternative materials are often complex, making them more expensive to manufacture.

While the art has focused on how to protect or substitute silver or silver chloride materials in biomedical electrodes, it has not provided a means to avoid corrosion altogether while continuing to use silver/silver chloride as conductive electrode materials. Some effort has been made to formulate conductive adhesives using antioxidants, for example. While such measures are intended to eliminate the corrosion problem, they have been less than effective, especially when "bicontinuous" adhesives having both hydrophilic and hydrophobic regimes are used. Therefore, a need remains for corrosion-resistant biomedical electrodes employing silver/silver chloride that are relatively easy to construct and remain relatively cost-effective.

While not intending to be bound by theory, it is known that peroxides are produced in conductive adhesives that are used to adhere biomedical electrodes to mammalian skin. The formation of peroxides is generally attributed to the process employed to "age" or condition the electrodes prior to use. It has been postulated that the formation of such peroxides is a factor in the onset of corrosion in biomedical electrodes, especially silver/silver chloride biomedical electrodes. In particular, the aging process for electrodes comprising bicontinuous conductive adhesives is believed to produce significant amounts of oxidizing peroxides because certain surfactants normally included in such adhesive formulations are abundant and of a type that can react to produce such peroxides.

It has now been unexpectedly discovered that a unique class of materials act as peroxide scavengers when used as additives in conductive adhesives, including bicontinuous adhesives, to significantly reduce the onset of corrosion in biomedical electrodes.

SUMMARY OF THE INVENTION

The present invention provides biomedical electrodes which, in one aspect, comprise a conductor in contact with a conductive medium, wherein the conductor comprises an electrically conductive surface comprising an active source of silver and the conductive medium is associated with a peroxide scavenger.

The electrically conductive surface may further comprise a polymer film associated with the silver, the silver being in a form selected from the group consisting essentially of metallic silver, silver chloride or combinations of the foregoing. The biomedical electrode typically will include a non-conductive backing having a first side comprising a first major surface and a second side comprising a second major surface with the electrically conductive surface associated with the second major surface of the non-conductive backing. Additionally, the conductive medium will generally be provided in the form of an electrically conductive pressure sensitive adhesive associated with the conductive substrate, and the electrically conductive pressure sensitive adhesive will typically comprise the at least one peroxide scavenger. Alternatively, the peroxide scavenger may be provided in a separate coating associated with the electrically conductive adhesive, or as a separate coating over the electrically conductive pressure sensitive adhesive.

Suitable adhesive for use as a electrically conductive pressure sensitive adhesive include those comprising a substantially non-porous, bicontinuous structure resulting from components comprising water, free radically (co)polymerizable ethylenically unsaturated polar hydrophilic or amphiphillic monomers or oligomers, optional water soluble initiator and optional water soluble additive. In one formulation, the electrically conductive pressure sensitive adhesive is formulated from components comprising acrylic acid, polyoxyethylene acrylate isooctyl acrylate, surfactant, propylene glycol, and polyacrylic acid having a molecular weight of approximately 550,000. The electrically conductive pressure sensitive adhesive useful herein will normally include a peroxide scavenger or peroxide scavenging agent (used interchangeably herein) as a part of the electrically conductive pressure sensitive adhesive to prevent the corrosion of silver electrode materials. Suitable peroxide scavengers typically will have at least one atom selected from the group consisting of sulfur, selenium, and tellurium. More specifically, suitable peroxide scavengers may be selected from the group consisting of methionine, thiodipropionic acid, and dilauryl thiodipropionate and mixtures of the foregoing. A release liner may be disposed over the electrically conductive pressure sensitive adhesive prior to the first use of the electrode.

In another aspect, the invention provides a biomedical electrode comprising: A non-conductive backing having a first side comprising a first major surface and a second side comprising a second major surface; an electrically conductive surface associated with the second major surface of the non-conductive backing; and an electrically conductive pressure sensitive adhesive associated with the electrically conductive surface, the electrically conductive pressure sensitive adhesive comprising a peroxide scavenger.

The non-conductive backing may comprise a tab portion and a pad portion, with the first major surface and second major surface shared by both the tab portion and the pad portion. At least a portion of the electrically conductive surface is disposed over the second major surface on the pad portion, with the electrically conductive pressure sensitive adhesive being associated with the electrically conductive surface on the pad portion. Other features of this aspect of the invention are as already described above.

In still another aspect, the invention provides a method for the manufacture of a biomedical electrode, comprising the steps of: preparing a subassembly comprising a non-conductive backing having a first side comprising a first major surface and a second side comprising a second major surface and an electrically conductive surface on the second major surface of the non-conductive backing, the electrically conductive surface comprising silver; and applying a conductive medium to the electrically conductive surface of the subassembly, the conductive medium comprising a peroxide scavenger.

In this aspect, applying a conductive medium may comprise formulating an electrically conductive pressure sensitive adhesive (as previously described) with peroxide scavenger and then applying the electrically conductive pressure sensitive adhesive to the electrically conductive surface. The step of preparing a subassembly may comprise applying a silver containing ink to the second major surface of the non-conductive backing to provide the electrically conductive surface. Another feature of this aspect of the invention includes the addition of the peroxide scavenger to the ink and applying the conductive adhesive over the ink. Still another feature of this aspect of the invention includes the application of a coating of a peroxide scavenger over the conductive surface with the electrically conductive pressure sensitive adhesive applied over the coating of peroxide scavenger.

These and other features of the present invention will be further described and will be understood by those of skill in the art upon further consideration of the remainder of the disclosure including the Detailed Description Of The Preferred Embodiment along with the accompanying drawings, the Examples and the appended claims.

BRIEF DESCRIPTION OF THE DRAWINGS

In describing the preferred embodiment, reference is made to the various Figures depicting features of the embodiment identified with reference numerals, wherein like numerals indicate like structures and wherein.

DETAILED DESCRIPTION OF THE PREFERRED EMBODIMENT

Figure 1:
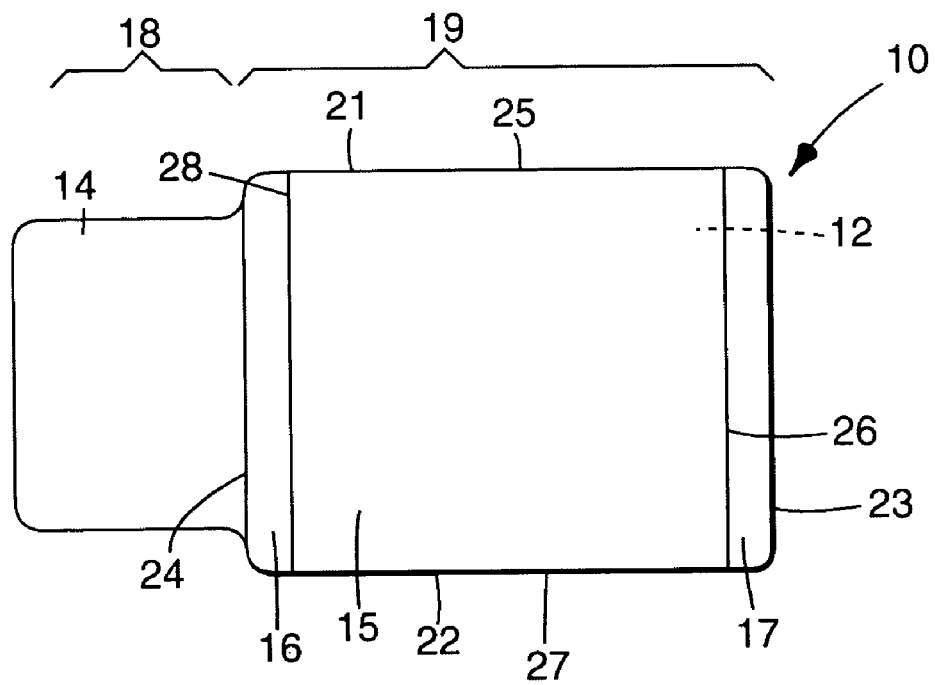
FIG. 1 is a bottom plan view of a diagnostic electrode according to the present invention.

The invention provides a biomedical electrode comprised of a conductor in contact with a conductive medium. The conductor includes a conductive substrate comprising silver and/or silver chloride. The conductive substrate may further comprise another material such as a polymeric material. The polymer or other material may be in the form of a thin film upon which the silver/silver chloride may be applied. The conductive substrate may comprise a graphite-loaded polymer or other conductive material in the form of a stud with a silver-containing layer disposed thereon. The silver-containing layer provides a source of silver and can be provided in any of a variety of forms such as, for example, a silver-containing ink, a vapor-deposited silver layer or another form of active silver. The silver in such a layer may be partially chlorided, either by having silver chloride intrinsic to the applied layer or by forming a chloride by an in situ chemical reaction of at least some of the silver associated with the layer. The conductor of the electrode is typically in contact with a conductive medium which may be provided in the form of a conductive adhesive, or as a conductive gel, for example. Other forms for the conductive medium may also be useful such as conductive pastes. A conductive adhesive may be provided in any of a variety of compositions such as those derived from polymerized microemulsions, polymerized mini-emulsions, hydrocolloids, hydrogels, and the like.

One or more peroxide scavengers or peroxide scavenging agents are associated with the conductive medium. The peroxide scavenger(s) may be water-soluble or an oil-soluble, depending on the form of the conductive medium. Peroxide scavengers will be understood to include any agent that effectively reduces the concentration of peroxide moieties to reduce and preferably eliminate the corrosion of the metals (e.g., silver) within the conductive substrate of a biomedical electrodes. Generally, the peroxide scavenging agents useful in the electrodes of the invention will comprise a material having at least one atom selected from sulfur, selenium, tellurium and/or combinations thereof.

As mentioned, the peroxide scavengers are selected to be compatible with the materials of the electrode while also being compatible with mammalian skin to which the electrode will be affixed. For compatibility with the materials of the electrode, the peroxide scavengers used in the present invention may be water soluble or oil soluble. Suitable water-soluble peroxide scavengers may be selected from any of a variety of materials such as, for example, compositions of methionine, thiodipropionic acid and combinations and derivatives thereof. Suitable oil-soluble peroxide scavengers also include any of a variety of materials including without limitation dilauryl thiodipropionate.

According to the present invention, at least one suitable peroxide scavenging agent should be associated with the conductive medium, such as a conductive adhesive, in an amount sufficient to diminish or arrest the corrosion. In the embodiments described herein, peroxide scavengers may be added to the formulations of conductive adhesives in concentrations that will typically be at least about 0.01 percent, more typically between about 0.01 percent and 5 percent by weight, based on the total weight of the conductive medium or adhesive, and often at a concentration of about 0.5 percent by weight of the conductive medium or adhesive.

Figure 2:
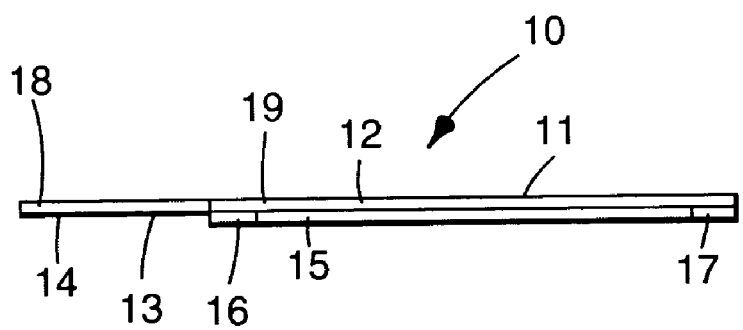
FIG. 2 is a side plan view of the diagnostic electrode of FIG. 1.

Referring now to the drawings, FIGS. 1 and 2 are bottom and side plan views, respectively, of one embodiment of a diagnostic electrode 10 according to the present invention. The view presented in FIG. 1 depicts the electrode 10 with a non-conductive backing 12 which will normally be made of flexible materials and positioned farthest away from mammalian skin when the electrode is in use. The non-conductive flexible backing 12 includes a first side 11 comprising a first major surface, and a second side 13 comprising a second major surface, the second major surface of side 13 is associated with an electrically conductive layer or surface 14 which is in contact with a conductive adhesive field 15. First and second non-conductive adhesive fields 16 and 17 of biocompatible pressure sensitive adhesive contact the second major surface of side 13 of the non-conductive backing 12 and as well as the electrically conductive surface 14. A release liner (not shown) may be placed in contact with the adhesive fields 15, 16, and 17 to protect the adhesive when the electrode 10 is not in use.

The non-conductive backing 12 comprises both a tab portion 18 and a pad portion 19. Both tab portion 18 and pad portion 19 are associated with the electrically conductive surface 14, while the field 15 of conductive adhesive is positioned to contact only pad portion 19. When the electrode 10 is in use, the tab portion 18 may serve to releasably attach an electrical connector that delivers ECG signals to the electrical instrumentation.

The pad portion 19 is bounded by a perimeter defined by the edges 21, 22, 23, and 24. By comparison, field 15 of conductive adhesive occupies a portion of the surface 13 of pad portion 19 with the conductive adhesive field being bounded by a perimeter defined by the edges 25, 26, 27, and 28. Hence, the surface area of conductive adhesive field 15 within edges 25–28 extends across the surface area of pad portion 19 within the edges 21–24 of pad portion 19.

First and second non-conductive adhesive fields 16 and 17 are positioned on the pad portion 19 in separate locations along the side 13 of the non-conductive backing 12 on the electrically conductive surface 14. The biocompatible pressure sensitive adhesive fields 16 and 17 are included in the construction of the described embodiment to assist in maintaining the adhesive contact of the electrode 10 to the skin of a patient. It will be appreciated that the invention is not limited to the described embodiment, and some embodiments may utilize the present invention but not require one or both of the fields 16 and 17.

In the embodiment of FIGS. 1 and 2, the fields 16 and 17 of biocompatible pressure sensitive adhesive are provided along opposing locations on pad portion 19 with respect to the field of conductive adhesive 15 and in a proximal and distal relationship to tab portion 18. The additional adhesion provided by the field 16 and 17 reinforces the adhesion of the electrode 10 to mammalian skin and helps to prevent delamination of the electrode along the edges 24 and 23, proximal and distal to the tab portion 18. As seen in FIG. 2, the biocompatible pressure sensitive skin adhesive fields 16 and 17 are associated with side 13 and generally in direct contact with the electrically conductive surface 14 of pad portion 19. The thickness of the pressure sensitive adhesive of adhesive fields 16 and 17 will generally range from about 0.25 mm to about 0.75 mm thick, and often will be about 0.50 mm thick. Typically, the thickness of fields 16 and 17 should be within 10% of one another and most typically will be substantially the same thicknesses and generally be substantially the same thickness as the conductive adhesive of field 15. In general, the fields 16 and 17 should be within 10 to 40 percent, of the final thickness of the ionically conductive adhesive of field 15. However, differences in the aforementioned thickness are still contemplated within the scope of the invention.

Figure 3:
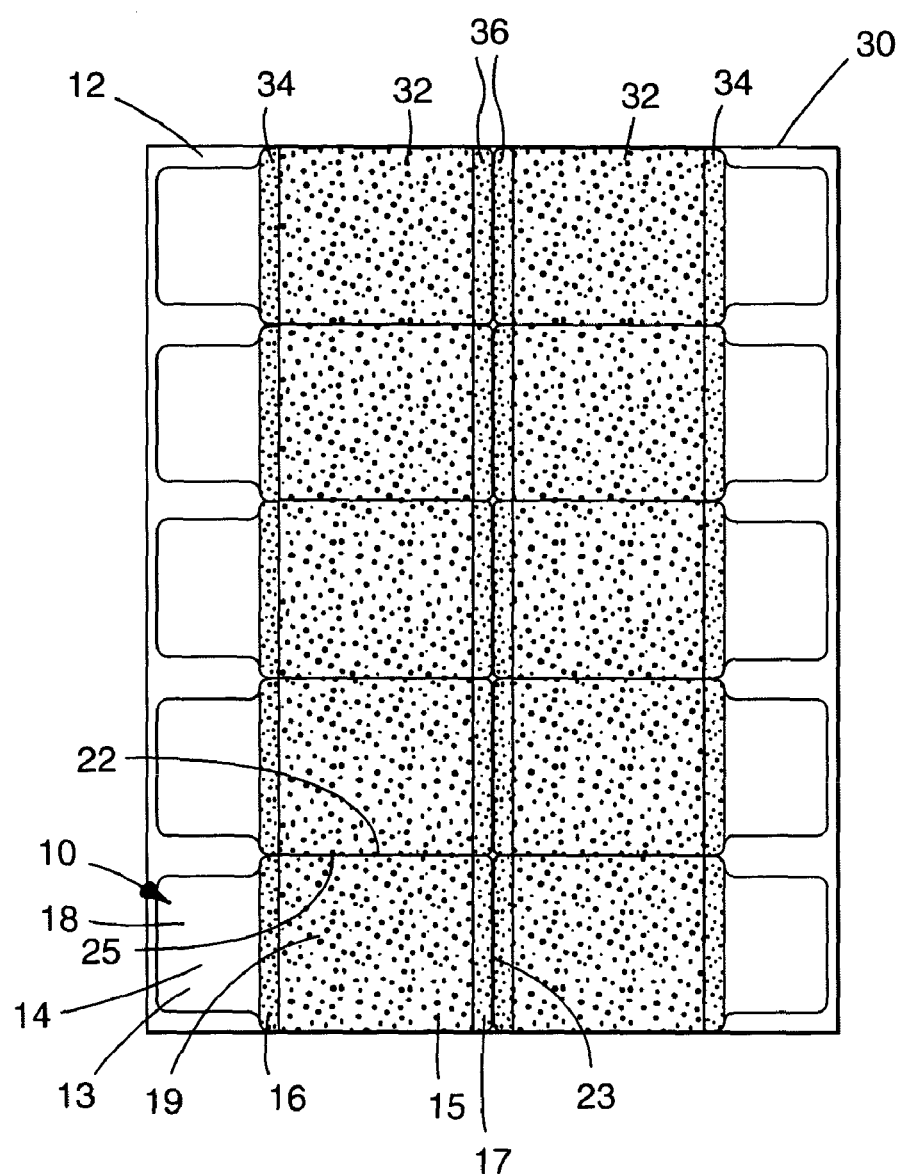
FIG. 3 is an array of diagnostic electrodes according to an embodiment of the invention during manufacture.

Referring now to FIG. 3, a method for the manufacture of electrodes 10 may be realized by use of a single sheet 30 constructed from the non-conductive backing material 12 and having electrically conductive surface 14 associated with the second major surface of the side 13. The sheet 30 is typically configured in a manner that permits it to be cut (e.g., die cut) into an array of electrodes 10 comprising tab portions 18 and pad portions 19, previously described. The edges 23 on each pad portion 19 distal to each tab portion 18 are aligned and contiguous. When cut, the depicted array of electrodes provides ten multiple individual electrodes 10. Of course, an array of any of a number of electrodes 10 can be arranged on a sheet such as single sheet 30 of the non-conductive backing 12, according to the present invention.

The combination of fields of adhesive 15, 16, and 17 can be coated from separate dies as contiguous stripes 32, 34, and 36, respectively, to provide on each pad portion 19 a field 16 of skin adhesive contacting electrically conductive surface 14 in a location proximal to tab portion 18, a field 15 of ionically conductive adhesive contacting electrically conductive surface 14 in a central area of pad portion 19 and a field 17 of skin adhesive contacting electrically conductive surface 14 in a location distal to tab portion 18. It will be appreciated that the coating width of adhesive stripe 36 will provide for field 17, and the width of the stripe 36 may be approximately twice the coating width of the adhesive stripe 34 for the non-conductive adhesive field 16. These differences in dimension will permit the single coating stripe 36 to provide two non-conductive adhesive fields 17, one for each of the electrodes resulting from cutting the non-conductive backing 12 along edge line 23 of the pad portions 19.

The coatings 32, 34, and 36 can be applied to result in any desired thickness, typically ranging from about 0.25 mm to about 0.75 mm and more typically from about 0.50 mm thick. For many applications, the final thickness of field 15 will not differ from the final thickness of fields 16 and 17 by more than about 20 percent different. Having coated stripes 32, 34, and 36 across each contiguous pad portion 19, the array of electrodes can be separated into individual electrodes by cutting between the adjoining edges 25 and 22 and between adjoining distal edges 23. In use, fields 16 and 17 of non-conductive biocompatible pressure sensitive skin adhesive provide adhesion to mammalian skin while conductive adhesive field 15, of similar final thickness to fields 16 and 17, receives electrical signals for ECG procedures, for example.

An alternative embodiment to electrode 10 can be constructed by providing only a single field 16 of biocompatible pressure sensitive skin adhesive adjoining field 15 of conductive adhesive and contacting electrically conductive surface 14 on pad portion 19. In this embodiment, field 17 of adhesive distal to tab portion is not utilized. However, the percentage differential final thickness between field 16 and field 15 would not be significantly different than in the embodiment shown in FIGS. 1 and 2.

The selection of suitable materials to construct electrode 10 is within the skill of those in the art of biomedical electrode construction. Any of a variety of materials are suitable, and exemplary materials for use in the construction of biomedical electrodes for ECG procedures may be found among those disclosed in U.S. Pat. No. 4,352,359 (Larimore); U.S. Pat. No. 4,524,087 (Engel); U.S. Pat. No. 4,539,996 (Engel); U.S. Pat. No. 4,554,924 (Engel); U.S. Pat. No. 4,848,348 (Carim); 4,848,353 (Engel); U.S. Pat. No. 5,012,810 (Strand et al.); U.S. Pat. No. 5,133,356 (Bryan et al.); U.S. Pat. No. 5,215,087 (Anderson et al.); U.S. Pat. No. 5,296,079 (Duan et al.); U.S. Pat. No. 5,385,679 (Uy et al.); U.S. Pat. No. 5,702,753 (Yasis et al.); U.S. Pat. No. 5,779,632 (Dietz et al), the disclosures of which are all incorporated herein by reference. Suitable electrically nonconductive materials for use as the backing material 12 include polymeric films and sheets, woven and nonwoven materials, and the like. In some embodiments, polyester films are useful and typically are of about 0.1 mm in thickness, such as those commercially available under the trade designation "Melinex" (e.g., 329 and 339) from ICI Americas of Hopewell, Va. These films may be treated with a corona treatment to improve the adhesion of the electrically conductive surface to the backing material.

Materials suitable for the electrically conductive surface 14 are numerous and will be known by those of skill in the art. In particular, inks containing electrical conductive particles such as graphite or metals are useful, with metal-containing inks being typically used. Particularly suitable inks are commercially available such as a silver containing ink available under the trade designation "N-30" ink, and a silver/silver chloride containing ink such as that known under the trade designation "R-300", or that known under the trade designation "R-301MPK (+240)", all commercially available from Ercon, Inc. of Waltham, Mass. Silver/silver chloride containing inks may be applied to the non-conductive backing material by any of a variety of known coating methods such as gravure coating, ink jet printing, silkscreen printing, knife coating, and the like.

Conductive adhesives for use in the adhesive field 15 may be selected from any of a variety of adhesives. The particular adhesive employed may comprise an essentially non-conductive adhesive formulated with a suitable conductive material to render it conductive, or it may comprise materials essential to the formulation of the adhesive that also inherently serve to provide the necessary conductive qualities for use in the electrodes of the invention. Suitable adhesive formulations foe the conductive adhesive include those described in the patent art, such as in the table in column 16 of U.S. Pat. No. 5,012,810 (Strand et al.) and as disclosed in U.S. Pat. Nos. 4,524,087; 4,539,996; 4,848,353; 4,554,924 (all Engel); U.S. Pat. No. 5,296,079 (Duan et al.); U.S. Pat. No. 5,385,679 (Uy et al.); U.S. Pat. No. 5,338,490 (Dietz et al.); U.S. Pat. No. 5,952,398; and 5,779,632 (Dietz et al.), the disclosures of which are all incorporated herein by reference. Particularly suitable adhesives include those described in the aforementioned '632 patent to Dietz et al., comprising a bicontinuous biocompatible conductive adhesive having interpenetrating domains of hydrophilic and hydrophobic compositions.

Another particularly useful adhesive for use as the conductive adhesive herein is the adhesive described in U.S. Patent Application 20020188035 to Uy et al., the disclosure of which is incorporated herein by reference. The disclosed adhesive comprises a polymerized microemulsion pressure sensitive adhesive ("PSA") with a substantially nonporous, bicontinuous structure to simultaneously provide the bulk properties of both hydrophilic polymers and hydrophobic polymer PSAs. Peroxide scavengers, described herein, may be added to the adhesive during its formulation. In particular, the above described water soluble peroxide scavengers are most suitable for inclusion in the formulation of the conductive adhesive described by Uy et al. which will now be described in further detail.

The Uy et al. conductive adhesive comprises a number of components including as an aqueous phase comprising water, free radically (co)polymerizable ethylenically unsaturated polar hydrophilic or amphiphilic monomer(s) or oligomer(s), optional water soluble initiator, and optional water soluble additive to form a microemulsion PSA. The microemulsion compositions useful as in formulating conductive adhesives are formulated with an aqueous phase from starting materials which generally comprise from about 2 to about 50 percent by weight of water (e.g., deionized water), typically about 5 to about 30 percent by weight, and often about 6 to about 25 percent by weight, based upon the total weight of the microemulsion. The aqueous phase may also include water-soluble and/or water-dispersible additives selected for properties of the PSA in ultimate usage. To determine the most appropriate weight percent of water to be included in the microemulsion, the water can be added incrementally until a clear microemulsion region is reached.

In addition to water, the aqueous phase of the conductive adhesive comprises at least one free-radically polymerizable ethylenically-unsaturated polar monomer or oligomer. The polar monomers or oligomers can be oil insoluble (hydrophilic) or can be both water soluble and oil soluble (amphiphilic). Use of polar oligomers in the aqueous phase promotes formation of a substantially nonporous bicontinuous structure for the polymerized microemulsion PSA. Monomers are generally selected from the group consisting of polar monomers which are substantially insoluble in the oil phase and polar monomers other than oil-insoluble monomers (i.e., polar monomers which are both water soluble and oil soluble).

The microemulsion PSA compositions will cumulatively comprise from about 2 to about 90 percent by weight of the required hydrophilic or amphiphilic monomers or oligomers, generally from about 5 to about 70 percent by weight, and typically from about 10 to about 60 weight percent, based upon the total weight of the microemulsion. Exact weight percentages of the monomers may be varied to provide desired properties in the polymerized microemulsion PSA.

Useful polar ethylenically-unsaturated free-radically (co)polymerizable oligomers which are substantially insoluble in the oil phase or which are both water soluble and oil soluble include but are not limited to polyethylene oxide acrylates, polyethylene oxide diacrylates, polyethylene glycol acrylates, polyethylene glycol diacrylates, polyurethane acrylates, polyurethane diacrylates, N-vinylpyrrolidone macromer, and mixtures thereof. Particularly suitable polar ethylenically-unsaturated free-radically (co)polymerizable oligomers include polyethylene oxide acrylates and diacrylates. Useful oligomers generally have a number average molecular weight of about 100 to about 100,000, typically about 100 to about 60,000, and most often about 100 to about 5000. While the invention is not limited to oligomers having the aforementioned molecular weights, these molecular weight ranges generally provide desired physical properties (e.g., water absorption, porosity, strength) in the conductive adhesive.

A first type of optional polar monomer for inclusion in the aqueous phase is a water-soluble free-radically (co)polymerizable ethylenically-unsaturated polar monomer that is substantially oil insoluble in that the monomer has a solubility of less than about 0.5% by weight in the oil phase and exhibits a distribution ratio at a given temperature (preferably about 25° to 35° C.) of concentration in the oil phase to concentration in the aqueous phase of less than about 0.005. Such a monomer may be nonionic, e.g., acrylamide, or may be ionic. Mixtures of nonionic and ionic monomers may be used. Ionic monomers conforming to these criteria include but are not limited to sodium styrene sulfonate, potassium acrylate, sodium acrylate, sodium methacrylate, ammonium acrylate, sodium 2-acrylamido-2-methylpropane sulfonate, 4,4,9-trimethyl-4-azonia-7-oxa-dec-9-ene-1-sulfonate, N,N-dimethyl-N-(beta-methacryloxyethyl)ammonium propionate betaine, trimethylamine methacrylamide, 1,1-dimethyl-1-(2,3-dihydroxypropyl) amine methacrylamide, and other zwitterionic ethylenically-unsaturated monomers having the requisite solubility requirements, mixtures thereof, and the like. Particular suitable oil-insoluble polar monomers include those selected from the group consisting of acrylamide, sodium styrene sulfonate, sodium acrylate, sodium 2-acyrlamido-2-methylpropane sulfonate, sodium methacrylate, and mixtures thereof, due to ease of formulation and desirable properties when polymerized.

Many polar monomers known in the art exhibit some solubility in both water and oil. They can have a solubility of about 0.5% or greater in the oil phase and exhibit a distribution ratio at a given temperature (preferably about 25° C. to 30° C.) of concentration in the oil phase to a concentration in the aqueous phase of greater than or equal to about 0.005. Useful polar ethylenically-unsaturated free-radically (co)polymerizable monomers partitionable between the aqueous phase and the oil phase of the adhesive microemulsion include but are not limited to N-vinylpyrrolidone, N-vinylcaprolactam, (meth)acrylic acid, hydroxyethyl (meth)acrylate, itaconic acid, styrene sulfonic acid, N-substituted acrylamides, N,N-disubstituted acrylamides, N,N-dimethylaminoethyl methacrylate, 2-acrylamido-2-methyl propane sulfonic acid, and mixtures thereof. Preferred polar partitionable monomers include (meth)acrylic acid, N-vinylpyrrolidone, N-vinylcaprolactam, N,N-dimethylaminoethyl methacrylate, N,N-dimethylacrylamide, styrene sulfonic acid, 2-acrylamido-2-methyl propane sulfonic acid, and mixtures thereof. Most suitable polar partitionable monomers include acrylic acid, N-vinylpyrrolidone, N-vinylcaprolactam, N,N-dimethylacrylamide, and mixtures thereof, because of the favorable properties, such as physical strength, they can impart to the biphasic polymer composite.

The aqueous phase may optionally further comprise a water-soluble free-radical polymerization initiator selected from the group consisting of thermal initiators, photoinitiators, and mixtures thereof.

Water-soluble photoinitiators useful in the present invention are photoinitiators which generate free radicals on exposure to electromagnetic (usually ultraviolet) radiation which act as initiators for the (co)polymerization of the hydrophilic monomer(s), the oleophilic monomer(s), the (co)polymerizable oligomers, and, when present, the (co)polymerizable surfactant as detailed below. Useful water-soluble photoinitiators include but are not limited to benzophenones substituted with an ionic moiety, a hydrophilic moiety or both; thioxanthones substituted with an ionic moiety, a hydrophilic moiety or both, and 4-substituted-(2-hydroxy-2-propyl)phenyl ketones, wherein the 4-substituent is an ionic or hydrophilic moiety. Such ionic or hydrophilic moieties include but are not limited to hydroxyl groups, carboxyl groups, and carboxylic acid salt groups. Useful water-soluble benzophenones include but are not limited to 4-trimethylaminomethyl benzophenone hydrochloride and benzophenone sodium 4-methanesulfonate. Useful water-soluble thioxanthones include but are not limited to 3-(2-hydroxy-3-trimethylaminopropoxy) thioxanthone hydrochloride, 3-(3-trimethylaminopropoxy) thioxanthone hydrochloride, thioxanthone 3-(2-ethoxysulfonic acid) sodium salt, and thioxanthone 3-(3-propoxysulfonic acid) sodium salt. Useful water-soluble phenyl ketones include but are not limited to (2-hydroxy-2-propyl) (4-diethylene glycol phenyl) ketone, (2-hydroxy-2-propyl) (phenyl-4-butanecarboxylate) ketone, 4-(2-hydroxethoxy) phenyl-(2-propyl) ketone, and their water-soluble salts. A particularly suitable water-soluble photoinitiator is 4-trimethylaminomethyl benzophenone hydrochloride.

The aqueous phase may comprise about 0.05 to about 1 part by weight of a photoinitiator, and typically about 0.1 to about 1 part by weight based on 100 parts by weight of total (co)polymerizable species in the microemulsion. Suitable water-soluble initiators include those which, on exposure to heat, generate free-radicals that initiate (co)polymerization of the hydrophilic monomer(s), the oleophilic monomer(s), the (co)polymerizable oligomer and, when present, the (co)polymerizable surfactant, as detailed below. Suitable water-soluble thermal initiators include but are not limited to potassium persulfate, ammonium persulfate, sodium persulfate, and mixtures thereof; oxidation-reduction initiators such as the reaction product of the above-mentioned persulfates and reducing agents such as sodium metabisulfite and sodium bisulfite; and 4,4'-azobis(4-cyanopentanoic acid) and its soluble salts (e.g., sodium, potassium). A particularly suitable water-soluble thermal initiator is ammonium persulfate. Generally, water-soluble thermal initiators are used at temperatures of from about 50° to about 70° C., while the oxidation-reduction-type initiators are used at temperatures of from about 30° to about 50° C. When used, water-soluble thermal initiators may comprise from about 0.05 to about 1 part by weight, typically about 0.1 to about 1 part by weight based on 100 parts by weight of (co)polymerizable species in the microemulsion composition.

The aqueous phase may optionally further comprise various water-soluble additive(s) in order to produce a polymerized microemulsion PSA having specific properties and/or appearance. Each additive is selected to produce a desired end-product. For example, if a conductive polymer is desired, an electrolyte can be added. If a pigmented polymer is desired, a dye can be added. Examples of useful additives include but are not limited to water-soluble crosslinkers (such as methylene bisacrylamide), plasticizers (such as glycerin and polyalkylene glycols), pH adjusters, electrolytes, dyes, pigments, pharmaceutically-active compounds, physiologically-active compounds, cosolvents, noncopolymerizable polar oligomers, mixtures thereof, and the like. In particular, electrolytes including but not limited to potassium chloride, lithium chloride, sodium chloride, and mixtures thereof have been found to be useful in various formulations of the present invention when it is desired that the polymerized microemulsion PSA exhibit electrical conductivity. Up to about 10 parts by weight of an electrolyte can be included, preferably about 0.5 parts by weight to about 5 parts by weight based on 100 parts by weight of the total aqueous phase.

Noncopolymerizable polar oligomers useful as additives include but are not limited to poly(N-vinylpyrrolidone), polyethylene glycols, poly(oxyethylene) alcohols, poly(ethylimine), and mixtures thereof. Such oligomers are added to affect the bulk properties of the resulting polymerized microemulsion PSA, e.g. to impart hydrophilic properties to the material.

Typical cosolvents include aliphatic alcohols having from about 1 to about 8 carbon atoms (such as glycerin), polyethers (such as those available under the trade designations Butyl Cellosolve, Butyl Carbitol, Hexyl Cellosolve, and Hexyl Carbitol commercially available from Union Carbide), and mixtures thereof.

It will be recognized that organic water soluble additives which are added to the aqueous phase will exhibit degrees of solubility in the organic phase of the microemulsion. Each additive has its own distribution ratio between the aqueous phase and the organic phase.

The terms "organic phase", "oil phase", and "lipophilic phase" are used interchangeably herein.

Prior to commencing polymerization, the oil phase of the microemulsion compositions of the invention generally comprises hydrophobic free-radically (co)polymerizable monomers suitable for forming a hydrophobic pressure sensitive adhesive homopolymer or copolymer, free radically (co)polymerizable polar monomer, oil-soluble initiator, and optional reactive lipophilic additives.

Hydrophobic free-radically (co)polymerizable monomers useful in the lipophilic phase of the microemulsion PSAs include ethylenically-unsaturated monomers selected from the group consisting of about $C_1$ to about $C_{18}$ alkyl esters of acrylic acid, i.e., those esters derived from acrylic acid and about $C_1$ to about $C_{18}$ alcohols, provided that such monomers are suitable for forming a hydrophobic polymer having pressure sensitive adhesive properties.

The glass transition temperature ($T_g$) of the resulting polymerized microemulsion PSA is influenced by the selection of hydrophobic monomers suitable for forming a hydrophobic polymer having pressure sensitive adhesive properties. A $T_g$ of less than about 10° C. will frequently provide a resulting hydrophobic polymer having pressure sensitive adhesive properties. A $T_g$ of less than about 0° C. will more frequently provide a resulting hydrophobic polymer having pressure sensitive adhesive properties. A $T_g$ of less than about −10° C. will most frequently provide a resulting hydrophobic polymer having pressure sensitive adhesive properties. Of possible hydrophobic monomer candidates, alkyl acrylates, including isooctyl acrylate, 2-ethylhexyl acrylate, and n-butyl acrylate, are particularly useful due to their commercial availability and because of the relatively low $T_g$ of the resulting hydrophobic polymer formed from such hydrophobic monomers.

The organic phase may further optionally comprise free-radically polymerizable ethylenically-unsaturated comonomers which are copolymerizable with the alkyl acrylate monomers described above in order to modify the glass transition temperature ($T_g$) of the resulting polymerized microemulsion PSA, from that $T_g$ contributed by the hydrophobic monomer(s). Suitable comonomers include styrene, acrylonitrile, and vinyl esters (such as vinyl acetate, vinyl propionate and vinyl neopentanoate, etc.) with the selection of the comonomer dependent on the properties desired of the final solid bicontinuous polymer.

The polymerized microemulsion PSAs generally comprise from about 5 to about 80 percent by weight of hydrophobic monomers, typically from about 10 to about 70 percent by weight, and often from about 12 to about 60 percent by weight based on the total weight of the microemulsion, to impart sufficient strength, cohesiveness, and pressure sensitive adhesive properties to the resulting polymerized microemulsion PSA.

The oil phase further comprises an oil-soluble free-radical photoinitiator and optionally further comprises a thermal initiator. Useful oil-soluble photoinitiators generally include those that generate free radicals on exposure to electromagnetic (usually ultraviolet) radiation which act as initiators for the (co)polymerization of the hydrophilic monomer(s) and/or oligomer(s), the oleophilic monomer(s), and, when present, the (co)polymerizable surfactant. Useful photoinitiators include, but are not limited to: (1) mixtures of Michler's ketone and benzil or benzophenone, generally in a weight ratio of about 1:4; (2) coumarin-based photoinitiator systems as described in U.S. Pat. No. 4,289,844, incorporated by reference herein; and (3) systems based on dimethoxyphenylacetophenone and/or diethoxyacetophenone. The oil-soluble photoinitiators are initially included in the microemulsions as part of the organic phase. On irradiation, the free-radicals thus generated effect (co)polymerization of monomers in both the aqueous and the organic phases, as well as copolymerization of the (co)polymerizable surfactant. The organic phase generally comprises about 0.01 to about 5 parts by weight of an oil soluble photoinitiator, based on 100 parts by weight of total (co)polymerizable species in the microemulsion.

Oil-soluble thermal initiators may optionally be used in the preparation of the bicontinuous polymers of the present invention in order to complete the polymerization reaction subsequent to the photopolymerization step described above. Useful oil-soluble thermal initiators include those that, on exposure to heat, generate free radicals which initiate (co)polymerization of the hydrophilic monomer(s), oligomer(s) the oleophilic monomer(s), and, when present, the polymerizable surfactant, as detailed below. Suitable oil-soluble thermal initiators include but are not limited to those selected from the group consisting of azo compounds such as Vazo 64™ (2,2'-azobis(isobutyronitrile) and Vazo 52™ (2,2'-azobis(2,4-dimethylpentanenitrile)), both available from duPont, peroxides such as benzoyl peroxide and lauroyl peroxide, and mixtures thereof. A preferred oil-soluble thermal initiator is (2,2'-azobis(isobutyronitrile)). The organic phase may comprise about 0 to about 5 parts by weight of an oil-soluble thermal initiator, typically about 0.05 to about 5 parts by weight when used, often about 0.1 to about 5 parts if used, based on 100 parts of total weight of (co)polymerizable compounds in the microemulsion.

The organic phase may optionally further comprise one or more additional free-radically reactive constituents, including, but not limited to oil-soluble crosslinking agents, chain transfer agents, and mixtures thereof. Examples of useful crosslinking agents include but are not limited to those selected from the group consisting of divinylbenzene; about $C_4$ to about $C_8$ alkyl diacrylates such as 1,4-butanediol diacrylate, 1,6-hexanediol diacrylate, 1,8-octanediol diacrylate; and mixtures thereof. One suitable crosslinking agent is 1,6-hexanediol diacrylate. The crosslinking agent, if added, will change the physical properties, such as cohesive strength, of the final adhesive polymer. The organic phase optionally further comprise about 0 to about 10 or more, parts by weight crosslinker, typically, if used, about 0.1 to about 2 percent by weight, based on 100 parts by weight of the total oil phase. The amount of crosslinker used will determine the physical properties of the polymer, such as insolubility in solvents, modulus, and internal strength. For such applications, the organic phase typically comprises about 0.1 to about 5 parts by weight of a crosslinker, based on 100 parts by weight of the oil phase.

The organic phase may optionally further comprise a chain transfer agent. Examples of useful chain transfer agents include carbon tetrabromide, alcohols, mercaptans, and mixtures thereof. One suitable chain transfer agent is isooctylthioglycolate. The oil phase may further comprise up to about 0.5 parts by weight of a chain transfer agent, typically about 0.01 weight percent to about 0.5 parts by weight, if used, often about 0.05 parts by weight to about 0.2 parts by weight, based upon 100 parts by weight of the total oil phase.

The oil phase may optionally further comprise one or more nonreactive oil-soluble additives. A variety of nonreactive oil-soluble additives may be included in the microemulsion. These materials are added to produce a final polymer system with specified physical properties or appearance. Examples of such optional oleophilic additives include one or more plasticizers, such as phthalate esters, for example. Plasticizer(s) may comprise about 0 to about 20 parts by weight, typically about 5 to about 20 parts by weight if used, more typically about 8 to about 15 weight percent based on 100 parts by weight of the oil phase.

Nonionic and ionic (anionic and cationic) surfactants are generally also employed in the conductive adhesive. The surfactant(s) may or may not be copolymerizable with the monomers of the conductive adhesive. Copolymerizable surfactant(s) may be desired to render the resulting adhesive less sensitive to water. When resistance to water is not required, noncopolymerizable surfactants are suitable and may be desired due to their generally lower cost.

Nonionic surfactants are usually condensation products of an organic aliphatic or alkylaromatic hydrophobic compound and an alkylene oxide, such as ethylene oxide, which is hydrophilic. Almost any hydrophobic compound having a carboxy, hydroxy, amido, or amino group with a free hydrogen present can be condensed with ethylene oxide to form a nonionic surfactant. The length of the ethylene oxide chain of the condensation product can be adjusted to achieve the desired balance between the hydrophobic and hydrophilic elements (Hydrophilic-Lipophilic Balance or HLB). The HLB of a surfactant is an expression of the balance of the size and strength of the hydrophilic (water-loving or polar) and the lipophilic (oil-loving or non-polar) groups of the surfactant. The useful HLB of nonionic surfactants for the present invention to prepare microemulsions is from about 6 to about 19, typically from about 9 to about 18, and most often from about 10 to about 16. Useful nonionic surfactants include non(co)polymerizable nonionic surfactants, ethylenically-unsaturated copolymerizable nonionic surfactants, and mixtures thereof.

Suitable nonreactive nonionic surfactants include condensation products of a higher aliphatic alcohol, such as a fatty alcohol, containing about 8 to about 20 carbon atoms, in a straight or branched chain configuration, condensed with about 3 to about 100 moles, typically about 5 to about 40 moles, most often about 5 to about 20 moles of ethylene oxide to achieve the above defined HLB. Examples of such nonionic ethoxylated fatty alcohol surfactants are those that include $C_{11}$–$C_{15}$ secondary alcohol polyethyleneglycol ethers such as those available under the trade designation Tergitol 15-S from Union Carbide and surfactants comprising polyoxyethylene(20) cetyl ether and polyoxyethylene (10) stearyl ether, such as those available under the trade designations Brij 76 and Brij 58, commercially available from ICI.

Other suitable nonreactive nonionic surfactants include polyethylene oxide condensates of one mole of alkyl phenol containing from about 6 to 12 carbon atoms in a straight or branched chain configuration, with about 3 to about 100 moles, typically about 5 to about 40 moles, most typically about 5 to about 20 moles of ethylene oxide to achieve the above defined HLB. Examples of nonreactive nonionic surfactants are surfactants that include nonylphenoxy poly (ethyleneoxy) ethanols such as those available under the trade designation "Igepal" from Rhone-Poulenc, especially ther CO and CA series surfactants. Igepal CA surfactants include octylphenoxy poly(ethyleneoxy) ethanols.

Another group of usable nonreactive nonionic surfactants include block copolymers of ethylene oxide and propylene oxide or butylene oxide with HLB values of about 6 to about 19, typically about 9 to about 18, and most often about 10 to about 16. Examples of such nonionic block copolymer surfactants include ethylene oxide-propylene oxide block copolymers such as those commercially available under the trade designations "Pluronic" and "Tetronic" from BASF.

Still other satisfactory nonreactive nonionic surfactants include but are not limited to sorbitan fatty acid esters, polyoxyethylene sorbitan fatty acid esters and polyoxyethylene stearates having HLBs of about 6 to about 19, generally about 9 to about 18, and most typically about 10 to about 16. Suitable commercially available fatty acid ester nonionic surfactants include thos available under the trade designations "Span", "Tween", and "Myrj" from ICI. The Span surfactants include $C_{12}$–$C_{18}$ sorbitan monoesters. The Tween surfactants include poly(ethylene oxide) $C_{12}$–$C_{18}$ sorbitan monoesters. The "Myrj" surfactants include poly (ethylene oxide) stearates.

Suitable nonionic surfactants for incorporation in the conductive adhesive microemulsion PSA are ethylenically-unsaturated copolymerizable nonionic surfactants including but not limited to those falling within the general formula:

$$R\!\!-\!\!O\!\!-\!\!(R'O)_m\text{-}(EO)_{(n-1)}\!\!-\!\!CH_2CH_2OH$$

where:

R is selected from the group consisting of (about $C_2$ to about $C_{18}$) alkenyl, acrylyl, acrylyl (about $C_1$ to about $C_{10}$) alkyl, methacrylyl, methacrylyl (about $C_1$ to about $C_{10}$) alkyl, vinylphenyl and vinylphenylene (about $C_1$ to about $C_6$) alkyl;

R'O is selected from the group consisting of bivalent alkyleneoxy groups derived from epoxy compounds having more than two carbon atoms, preferably three or four carbon atoms, such propylene oxide, butylene oxide, etc. and combinations thereof;

E is a bivalent ethylene radical;

m represents an integer of about 5 to about 100;

n represents an integer of about 5 to about 100; the ratio of m and n being from about 20:1 to about 1:20.

It will be understood that varying the ratio of m and n will vary the HLB of the polymerizable surfactant. The required HLB for the nonionic surfactant(s) of the present invention is from about 6 to about 19, typically from about 9 to about 18, and most typically from about 10 to about 16. Examples of such copolymerizable nonionic surfactants are the alkylene polyalkoxy ethanol surfactants available from PPG Industries under the trade designations "Mazon BSN" 185, 186 and 187. Mazon BSN surfactants include alkylene polyalkoxy ethanol.

Anionic surfactants normally include a hydrophobic moiety selected from the group consisting of (about $C_6$ to about $C_{20}$) alkyl, alkylaryl, and alkenyl groups and an anionic group selected from the group consisting of sulfate, sulfonate, phosphate, polyoxyethylene sulfate, polyoxythylene sulfonate, polyoxethylene phosphate and the alkali metal salts, ammonium salts, and tertiary amino salts of such anionic groups. A particular ethylenically-unsaturated copolymerizable surfactant which includes (about $C_2$ to about $C_{18}$) alkenyl polyoxypropylene or (about $C_2$ to about $C_{18}$) polyoxybutylene as a hydrophobic moiety and an anionic group of polyoxyethylene sulfate is also useful.

Nonreactive anionic surfactants which can be used in the present invention include but are not limited to alkyl or alkylaryl sulfates or sulfonates (about $C_6$ to about $C_{20}$) such as sodium lauryl sulfate (commercially available under the trade designation Polystep B-3 from Stepan Co.) and sodium dodecyl benzene sulfonate, (commercially available under the trade designation Siponate DS-10 from Rhone-Poulenc); polyoxyethylene (about $C_6$ to about $C_{20}$) alkyl or alkylphenol ether sulfates with the ethylene oxide repeating unit in the surfactant below about 30 units, typically below about 20 units, most often below about 15 units, such as those available under the trade designation Polystep B-1 from Stepan Co. and Alipal EP110 and 115 from Rhone-Poulenc; (about $C_6$ to about $C_{20}$) alkyl or alkylphenoxy poly(ethyleneoxy)ethyl mono-esters and di-esters of phosphoric acid and its salts, with the ethylene oxide repeating unit in the surfactant below about 30 units, typically below about 20 units, most often below about 15 units, such as those available under the trade designations Gafac PE-510 and Gafac RE-610 from GAF.

Suitable anionic surfactants for incorporation in the microemulsion compositions include but are not limited to ethylenically-unsaturated copolymerizable surfactants of the formula:

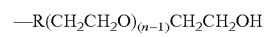

where:

R is selected from the group consisting of about $C_2$ to about $C_{18}$ alkenyl, acrylyl, acrylyl (about $C_1$ to about $C_{10}$) alkyl, methacrylyl, methacrylyl (about $C_1$ to about $C_{10}$) alkyl, vinylphenyl and vinylphenylene (about $C_1$ to about $C_6$) alkyl;

R'O is selected from the group consisting of bivalent alkyleneoxy groups derived from epoxy compounds having more than two carbon atoms, preferably three or four carbon atoms, such as propylene oxide and butylene oxide and mixtures of such alkyleneoxy groups;

E is a bivalent ethylene radical;

m represents an integer of about 5 to about 100;

n represents an integer of about 5 to about 100; the ratio of m and n being from about 20:1 to about 1:20.

It will be understood that varying the ratio of m and n will vary the HLB of the polymerizable surfactant. The required HLB for the anionic copolymerizable surfactants of the present invention, exclusive of the X-group, is from about 3 to about 16. X is an anionic group selected from the group consisting of sulfonate, sulfate, phosphate, and alkali metal salts or ammonium salts or tertiary amino salts of such anionic groups. An example of such a copolymerizable anionic surfactant that available under the trade designation Mazon SAM 211 from PPG Industries, Inc.

Cationic surfactants useful in the present invention include but are not limited to quaternary ammonium salts in which at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate etc.). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One or more of the substituents may include an aryl moiety or may be replaced by an aryl, such as benzyl or phenyl. Among the possible lower molecular weight substituents are also lower alkyls of about 1 to about 4 carbon atoms, such as methyl and ethyl, substituted by lower polyalkoxy moieties such as polyoxyethylene moieties, bearing a hydroxyl end group, and falling within the general formula:

where R is a $C_1$ to $C_4$ divalent alkyl group bonded to the nitrogen, and n represents an integer of about 1 to about 15. Alternatively, one or two of such lower polyalkoxy moieties having terminal hydroxyls may be directly bonded to the quaternary nitrogen instead of being bonded to it through the previously mentioned lower alkyl. Examples of useful quaternary ammonium halide surfactants for use in the present invention include but are not limited to methyl-bis(2-hydroxyethyl)coco-ammonium chloride or oleyl-ammonium chloride, (commercially available under the trade designations Ethoquad C/12 and O/12, respectively) and methyl polyoxyethylene (15) octadecyl ammonium chloride (commercially available under the trade designation Ethoquad 18/25) from Akzo Chemical Inc.

Thickening agents useful in the present invention include hydrophilic polymers formed partially or completely from acrylic acid monomer. Homopolymers of acrylic acid are generally considered suitable, although hydrophilic copolymers of acylic acid, such as those containing at least about 20%, and typically at least 80%, residues of acrylic acid, are also considered useful. The molecular weight of the thickening agent may be between about 200,000 and 800,000, with 400,000 to 700,000 being especially suitable.

Regarding the biocompatible skin adhesives useful in the adhesive fields 16 and 17, discussed above, acrylate pressure sensitive adhesives and tackified polystyrene-polyisoprene block copolymers pressure sensitive adhesives are suitable. Such acrylate ester copolymer adhesives are generally described in U.S. Pat. Nos. 2,973,286; Re 24,906; Re 33,353; 3,389,827; 4,112,213; 4,310,509; 4,323,557; 4,732, 808; 4,917,928; 4,917,929; and European Patent Publication 0 051 935, the disclosures of which are all incorporated herein by reference. Tackified block copolymer adhesives are generally described by Ewins in, "Thermoplastic Rubbers: A-B-A Block Copolymers" which is Chapter 13 of Satas, Ed., Handbook of Pressure Sensitive Adhesive Technology, Second Edition, Van Nostrand Reinhold, 1989, incorporated herein by reference. Use of tackified block copolymer adhesives as biocompatible skin adhesives in biomedical electrodes is described in U.S. Pat. No. 4,204,312.

A variety of coating methods are available for both the conductive adhesive and the biocompatible skin adhesive including extrusion coating, knife coating, and curtain coating as described in Satas, "Coating Equipment" which is Chapter 34 of Satas, Ed., Handbook of Pressure Sensitive Adhesive Technology, Second Edition, Van Nostrand Reinhold, 1989, which is incorporated herein by reference. Hand knife coating can be employed. A slot die is preferably used, which can include an extrusion die, a knife die, a curtain coating die and other types of slot dies with a high shear flat wiping lip, a medium shear flat wiping lip, a medium shear rod wiping lip, or a sharp knife wiping lip, which are generally described by Lippert in, "Slot Die Coating for Low Viscosity Fluids", which is Chapter 11 of Satas, Ed., Coatings Technology Handbook, Marcel Dekker, Inc., 1991, incorporated by reference herein. The choice of the coating method and use of slot dies depend on the nature of the adhesive precursor, whether it is a high viscosity 100% solids hot-melt, a moderate viscosity 100% solids material to be polymerized on-web, or a moderate to low viscosity solvent or water delivered material. One skilled in the art will recognize that in the latter case, the coating step includes a drying process and this drying process results in a final thickness of adhesive that is thinner than the thickness at the coating head due to loss of solvent or water. The final thickness of conductive adhesive should be within 40% of the final thickness of the biocompatible pressure sensitive adhesive in order for both types of adhesive to have contact with the skin of a patient.

EXAMPLES

Further aspects of the invention are described in the following non-limiting Examples.

Example 1

This example uses a water-soluble peroxide scavenger as an antioxidant incorporated in the synthesis of a microemulsion hydrogel adhesive. A microemulsion was prepared for use as a conductive adhesive according to the invention. The microemulsion was prepared in the manner generally disclosed in co-pending and co-assigned U.S. Patent Application 20020188035 to Uy et al. More specifically, a first mixture was formed by mixing quantities of two hydrophilic monomers, namely 14 grams of acrylic acid, with 14 grams of polyoxyethylene acrylate, commercially available under the trade designation "AM 90G" ester from Shin-Nakamura Chemical Co. Ltd. of Wakayama Japan. To this was added 14 grams of isooctyl acrylate as a hydrophobic monomer that was commercially obtained from e.g. Atofina Chemicals, Inc. of Philadelphia, Pa. To this was added 18 grams of a surfactant, commercially available under the trade designation "Brij 97" from Uniqema of New Castle, Del. Then, 0.5 grams of photoinitiator (commercially available under the trade designation "Irgacure 2959", from Ciba Gigy Corp.) was added to complete a first mixture.

A second mixture was then prepared by mixing 23 grams water, 1.2 grams potassium chloride, 10 grams of propylene glycol, and 0.5 grams of methionine, commercially available from Sigma Chemicals of Milwaukee, Wis. The methionine was included as a water-soluble peroxide scavenging agent. The first and second mixtures were combined together to form a microemulsion. To the microemulsion, a 17% aqueous polyacrylic acid solution having a molecular weight approximately 550,000, prepared from acrylic acid monomer, was added as a viscosity modifier. After the addition, the microemulsion remained clear and stable and the viscosity increased to approximately 200 cps, readily processable using conventional techniques.

The thickened microemulsion was then coated using a knife coater onto a release liner as substrate. The knife was set so that a 25 mil (0.64 mm) thick coating was obtained. Polymerization was induced in the coated microemulsion by exposure to ultraviolet radiation using a 350 Blacklight, commercially available from Sylvania of Danvers, Mass. A total dose of 1800 mJ/cm$^2$ was applied over approximately 7 minutes, forming a conductive, bicontinuous adhesive. This conductive adhesive had an excellent adhesion to human skin.

Several 1.0 square inch (6.5 cm$^2$) swatches of this adhesive were bonded to a conductive silver/silver chloride ink backing on one side and a release liner on the other side. The backing was made by coating a silver/silver chloride conductive ink solution commercially available under the trade designation "R300", from Ercon Inc. of Waltham, Mass., onto a polymeric backing made from 0.1 mm thick polyester film commercially available under the trade designation "Melinex 505" from ICI Films of Hopewell, Va., using a wire-coating procedure. The ink had a solids content of 58% by weight, of which the elemental silver comprised 70% by weight. The carrier solvent for the ink was methyl propyl ketone (MPK). The coated film was then dried at room temperature for 5 minutes followed by drying at 200° F. (93° C.) for 5 minutes.

Comparative Example A

This comparative example was made using the materials and the procedures of Example 1, with the exception that the methionine or peroxide scavenger was not included.

Example 1 and Comparative Example A

Figure 4:
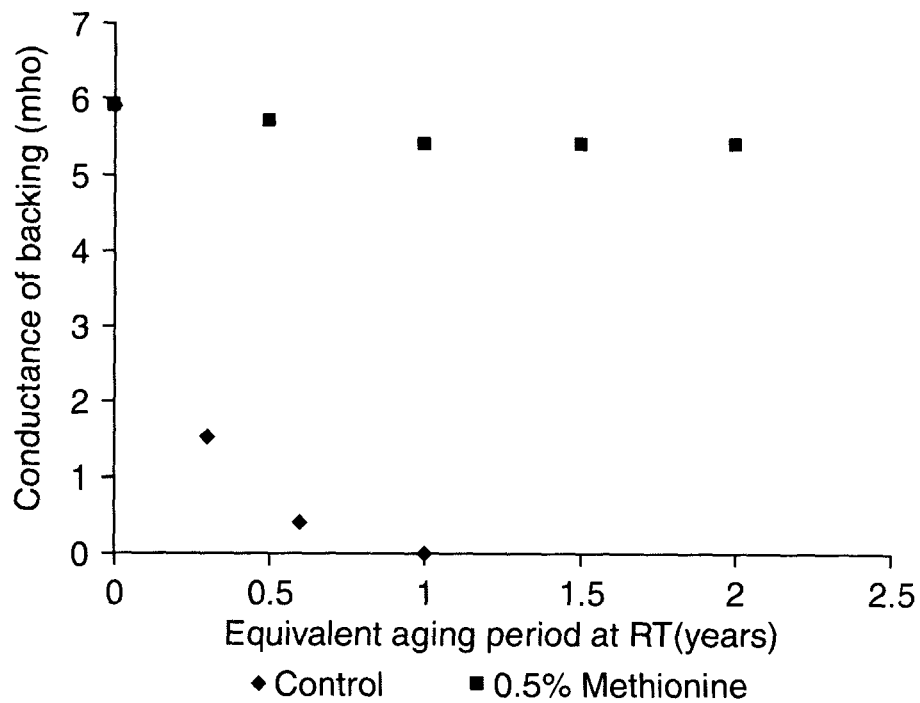
FIG. 4 is a graphical depiction of the results of an aging experiment.

The samples from Example 1 and Comparative Example A were individually sealed in foil pouches and aged at 150° F. for six weeks. Samples of the material of Example 1 as well as that of the Comparative Example A were removed at regular intervals and tested for corrosion by measuring the non-contact conductance of the backing. The conductance was measured using a Delcom 707 Conductance Monitor manufactured by Delcom Instruments Inc. of Prescott, Wis. The results are presented graphically in FIG. 4 where the Y-axis corresponds to the conductance of the backing in mhos while the X-axis corresponds to an equivalent aging period of the electrodes at room temperature (70° F.). This equivalent aging period is calculated by using the Vont Hoff rule, which states that the rate of a chemical reaction increases twofold for every 10° C. increase in temperature.

Example 2

An experimental sample was made using the procedure of Example 1, except that the peroxide scavenging agent methionine used in Example 1 was replaced by 0.5 grams of thiodipropionic acid, commercially available from Sigma Chemicals of Milwaukee, Wis.

Example 3

An experimental sample was made using the procedure of Example 1, except that the methionine was replaced by 0.5 grams of dilauryl thiodipropionate, commercially available from Sigma Chemicals of Milwaukee, Wis.

Examples 2 and 3 and Comparative Example A

Figure 5:
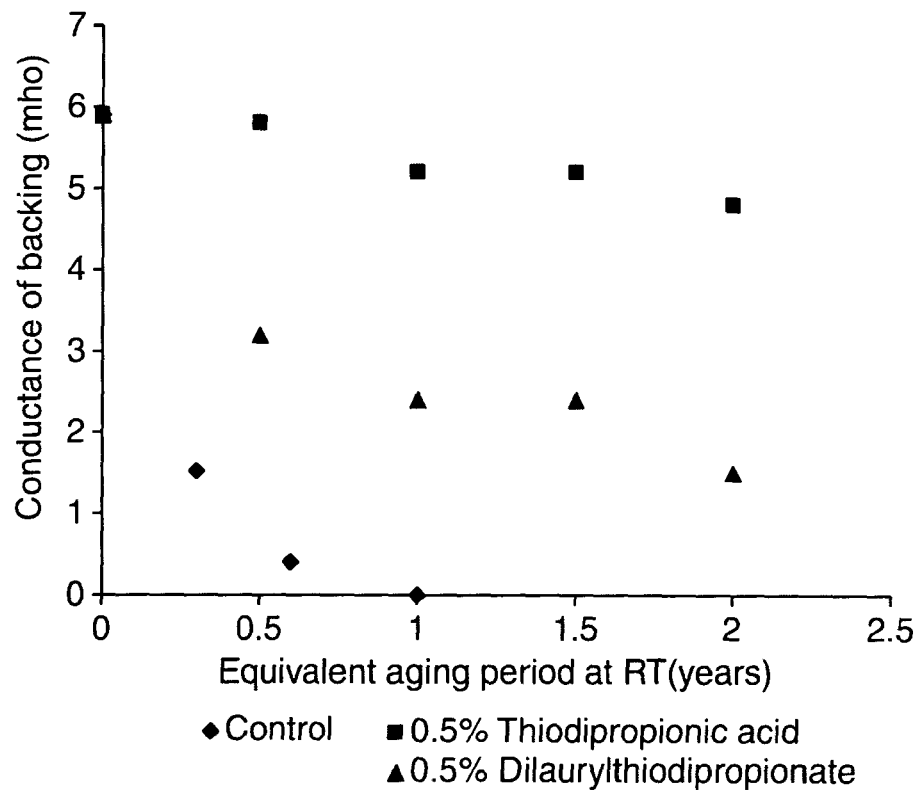
FIG. 5 is a graphical depiction of the results of another aging experiment.

The samples from Examples 2 and 3 were individually sealed in foil pouches and then aged and tested for conductance according to the procedure noted above in the comparison between Example 1 and Comparative Example A. The results are presented graphically in FIG. 5, along with the control data obtained for Comparative Example A. The Y-axis in FIG. 5 corresponds to the conductance of the backing in mhos while the X-axis corresponds to an equivalent aging period of the electrodes at room temperature (70° F.) calculated by using the Vont Hoff rule.

Comparative Example B

A comparative sample was made using the procedure of Example 1, except that the methionine was replaced by 0.5 grams of ascorbic acid, commercially available from Sigma Chemicals of Milwaukee, Wis. Ascorbic acid is a water-soluble antioxidant but not a peroxide scavenger.

Comparative Example C

A comparative sample was made using the procedure of Example 1, except that the methionine was replaced by 0.5 grams of butylated hydroxy toluene (BHT), commercially available from Sigma Chemicals of Milwaukee, Wis. Butylated hydroxy toluene is an oil-soluble antioxidant but is not a peroxide scavenger.

Comparative Examples B and C

Figure 6:
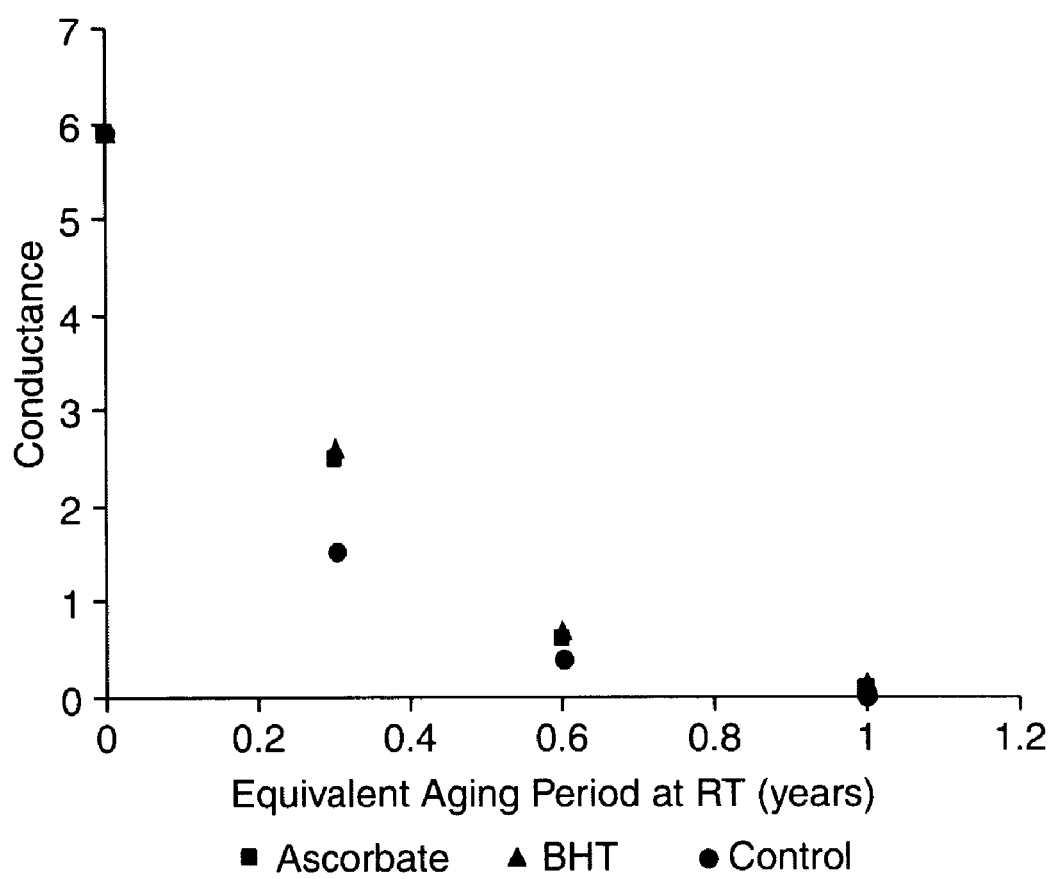
FIG. 6 is a graphical depiction of the results of still another aging experiment.

The samples from Examples B and C were individually sealed in foil pouches and then aged and tested for conductance according to the procedure described in the comparison between Example 1 and Comparative Example A. The results are presented graphically in FIG. 6, along with the control data from Comparative Example A. Note that the scale of the X-axis is different than those of FIGS. 4 and 5. The Y-axis corresponds to the conductance of the backing in mhos while the X-axis corresponds to an equivalent aging period of the electrodes at room temperature (70° F.) calculated by using the Vont Hoff rule.

While the preferred embodiment of the invention has been described in detail herein, it will be appreciated that insubstantial variations of the embodiment described and claimed herein may be possible. All such variations, including those that are unforeseeable at this time by those reasonably skilled in the art, are considered to be within the scope of the present invention.

What is claimed is:

1. A biomedical electrode comprising a conductor in contact with a conductive medium, wherein the conductor comprises an electrically conductive surface comprising an active source of silver and the conductive medium is associated with a peroxide scavenger selected from the group consisting of methionine, thiodipropionic acid, and dilauryl thiodipropionate and mixtures of the foregoing.

2. The biomedical electrode of claim 1 wherein the electrically conductive surface further comprises a polymer film associated with the silver, the silver being in a form selected from the group consisting essentially of metallic silver, silver chloride and combinations of the foregoing.

3. The biomedical electrode of claim 2 wherein the conductive surface comprises a graphite loaded polymer.

4. The biomedical electrode of claim 1 further comprising a non-conductive backing having a first side comprising a first major surface and a second side comprising a second major surface; the electrically conductive surface associated with the second major surface of the non-conductive backing; and the conductive medium comprising an electrically conductive pressure sensitive adhesive associated with the electrically conductive surface, the electrically conductive pressure sensitive adhesive comprising the at least one peroxide scavenger.

5. The biomedical electrode of claim 4 wherein the electrically conductive surface further comprises a polymer film associated with the silver, the silver being in a form selected from the group consisting essentially of metallic silver, silver chloride and combinations of the foregoing.

6. The biomedical electrode of claim 4 wherein the electrically conductive pressure sensitive adhesive comprises a substantially non-porous, bicontinuous structure resulting from components comprising water, free radically (co)polymerizable ethylenically unsaturated polar hydrophilic or amphiphilic monomers or oligomers, optional water soluble initiator, and optional water soluble additive.

7. The biomedical electrode of claim 4 wherein electrically conductive pressure sensitive adhesive comprises the peroxide scavenger in an amount of at least 0.01 percent by weight of the electrically conductive pressure sensitive adhesive.

8. The biomedical electrode of claim 4 wherein the peroxide scavenger is present in an amount between about 0.01 percent and 5 percent by weight of the electrically conductive pressure sensitive adhesive.

9. The biomedical electrode of claim 4 wherein the non-conductive backing further comprises a tab portion and a pad portion, the first major surface and second major surface shared by the tab portion and the pad portion, at least a portion of the electrically conductive pressure sensitive adhesive being disposed over the second major surface on the pad portion, the electrically conductive pressure sensitive adhesive associated with the electrically conductive surface on the pad portion.

10. The biomedical electrode of claim 9 further comprising a first field and second field of non-conductive adhesives associated with the electrically conductive surface on the pad portion.

11. The biomedical electrode of claim 9 further comprising a release liner disposed over the electrically conductive adhesive.

12. The biomedical electrode of claim 4 wherein the electrically conductive pressure sensitive adhesive is formulated from components comprising acrylic acid, polyoxyethylene acrylate, isooctyl acrylate, surfactant, propylene glycol, and polyacrylic acid having a molecular weight of approximately 550,000.

13. The biomedical electrode of claim 1 wherein the conductor comprises a graphite loaded polymer in the form of a stud upon the outer surface of which is disposed a layer of partially chlorided silver.

14. A biomedical electrode comprising:
A non-conductive backing having a first side comprising a first major surface and a second side comprising a second major surface;
An electrically conductive surface associated with the second major surface of the non-conductive backing; and
An electrically conductive pressure sensitive adhesive associated with the electrically conductive surface, the electrically conductive pressure sensitive adhesive comprising a peroxide scavenger selected from the group consisting of methionine, thiodipropionic acid, and dilauryl thiodipropionate and mixtures of the foregoing.

15. The biomedical electrode of claim 14 wherein the electrically conductive surface comprises silver.

16. The biomedical electrode of claim 15 wherein electrically conductive surface further comprises a polymer film associated with the silver, the silver being in a form selected from the group consisting essentially of metallic silver, silver chloride and combinations of the foregoing.

17. The biomedical electrode of claim 14 wherein the electrically conductive pressure sensitive adhesive comprises a substantially non-porous, bicontinuous structure resulting from components comprising water, free radically (co)polymerizable ethylenically unsaturated polar hydrophilic or amphiphilic monomers or oligomers, optional water soluble initiator and optional water soluble additive.

18. The biomedical electrode of claim 14 wherein the peroxide scavenger is present in an amount of at least 0.01 percent by weight of the electrically conductive pressure sensitive adhesive.

19. The biomedical electrode of claim 14 wherein the peroxide scavenger is present in an amount between about 0.01 percent and 5 percent by weight of the electrically conductive pressure sensitive adhesive.

20. The biomedical electrode of claim 14 wherein the non-conductive backing further comprises a tab portion and a pad portion, the first major surface and second major surface shared by the tab portion and the pad portion, at least a portion of the electrically conductive surface being disposed over the second major surface on the pad portion, and the electrically conductive pressure sensitive adhesive associated with the electrically conductive surface on the pad portion.

21. The biomedical electrode of claim 20 further comprising a first field and second field of non-conductive adhesives associated with the electrically conductive surface on the pad portion.

22. The biomedical electrode of claim 20 further comprising a release liner disposed over the electrically conductive pressure sensitive adhesive.

23. The biomedical electrode of claim 14 wherein the electrically conductive pressure sensitive adhesive is formulated from components comprising acrylic acid, polyoxyethylene acrylate, isooctyl acrylate, surfactant, propylene glycol, and polyacrylic acid having a molecular weight of approximately 550,000.

24. A method for preparing a biomedical electrode, comprising the steps of:
preparing a subassembly comprising a non-conductive backing having a first side comprising a first major surface and a second side comprising a second major surface and an electrically conductive surface on the second major surface of the non-conductive backing, the electrically conductive surface comprising silver; and applying a conductive medium to the electrically conductive surface of the subassembly, the conductive medium comprising a peroxide scavenger selected from the group consisting of methionine, thiodipropionic acid, and dilauryl thiodipropionate.

25. The method according to claim 24 wherein applying a conductive medium comprises formulating an electrically conductive pressure sensitive adhesive comprising the peroxide scavenger and applying the electrically conductive pressure sensitive adhesive to the electrically conductive surface.

26. The method according to claim 25 wherein formulating an electrically conductive pressure sensitive adhesive comprises formulating the adhesive to comprise a substantially non-porous, bicontinuous structure resulting from components comprising water, free radically (co)polymerizable ethylenically unsaturated polar hydrophilic or amphiphilic monomers or oligomers, optional water soluble initiator, optional water soluble additive and peroxide scavenger.

27. The method according to claim 24 wherein the peroxide scavenger is present in an amount of at least 0.01 percent by weight of the conductive medium.

28. The method according to claim 24 wherein the peroxide scavenger is present in an amount between about 0.01 percent and 5 percent by weight of the conductive medium.

29. The method according to claim 25 wherein formulating an electrically conductive pressure sensitive adhesive comprises formulating the adhesive from components, the components comprising acrylic acid, polyoxyethylene acrylate, isooctyl acrylate, surfactant, propylene glycol, and polyacrylic acid having a molecular weight of approximately 550,000.

30. The method according to claim 24 wherein preparing a subassembly further comprises applying a silver containing ink to the second major surface of the non-conductive backing to provide the electrically conductive surface.

31. The method according to claim 30 wherein the silver is provided in a form selected from the group consisting of metallic silver, silver chloride, and combinations thereof.

* * * * *